United States Patent [19]

Kocache et al.

[11] Patent Number: 4,988,946

[45] Date of Patent: Jan. 29, 1991

[54] PARAMAGNETIC GAS MEASURING APPARATUS

[75] Inventors: Riad M. A. Kocache; Danny F. Holman, both of East Sussex, England

[73] Assignee: Servomex (UK) Ltd., England

[21] Appl. No.: 458,633

[22] PCT Filed: Jun. 20, 1989

[86] PCT No.: PCT/GB89/00689
§ 371 Date: Jan. 19, 1990
§ 102(e) Date: Jan. 19, 1990

[87] PCT Pub. No.: WO89/12821
PCT Pub. Date: Dec. 28, 1989

[51] Int. Cl.[5] ............... G01N 31/00; G01N 27/74; G01R 33/12
[52] U.S. Cl. ............................ 324/204; 73/25.02
[58] Field of Search ................. 324/204; 73/27 A

[56] References Cited

FOREIGN PATENT DOCUMENTS 2155753 10/1972 France.
1363337 10/1972 United Kingdom.

Primary Examiner—Walter E. Snow
Attorney, Agent, or Firm—Marjama & Pincelli

[57] ABSTRACT

A gas testing apparatus comprising a body (13, 14) defining a chamber (7), means (2, 3) for creating a magnetic field within the chamber in a first direction, a test body (20), means (19) for mounting the test body (20) for rotation about an axis parallel to the direction of the magnetic field, and gas inlet (9) and outlet (10) means for allowing gas flow through the chamber (7), characterised in that the gas inlet means (9) are arranged and disposed to supply gas to the chamber from two positions at opposite sides of the chamber whereby gas flow from each of the two positions will be parallel to the direction of the magnetic field but in opposition in order to minimize errors resulting from gas flow upon the test body. The chamber is of small volume i.e. less than 0.6 ml which enables the apparatus to be used for preliminary monitoring.

8 Claims, 3 Drawing Sheets

PARAMAGNETIC GAS MEASURING APPARATUS

The invention relates to apparatus for the detection of gases, and in particular to gas testing apparatus utilising the magnetic susceptibility properties of gases for detection thereof, for example, gaseous oxygen.

Faraday showed, in the last century, that all matter was magnetic, that is either attracted or repelled by a magnetic field. This property, magnetic susceptibility is classified as diamagnetism when matter is repelled by a magnetic field and paramagnetism when it is attracted by a magnetic field. Faraday and others later built sensitive balances to measure these forces in gases. Most gases were found to be diamagnetic, however some gases such as oxygen, nitric oxide and nitrogen dioxide were found to be paramagnetic and hence attracted to a magnetic field. Oxygen in particular has a very strong paramagnetic property.

Two main types of magnetic balances were developed: ones using a uniform magnetic field (GOUY) and ones using a non uniform magnetic field based on the original Faraday design e.g. (Selwood). These were and still are very sensitive, bulky and very delicate laboratory instruments that require large electromagnets. The need to measure oxygen in the labs and in industry lead to the emergence of apparatus which utilised the strong paramagnetic property of oxygen to measure its concentration in a gas mixture of mainly diamagnetic gases. Different methods were developed.

Amongst the most succesful was one based on the Faraday gas susceptibility balance. This is basically a very sensitive torsion balance with a body which has a well defined shape and is made from a stable diamagnetic material such as quartz and filled with a diamagnetic gas such as nitrogen. The body is suspended in a strong and nonuniform magnetic field and the area immediately around it is enclosed and defined by a chamber in which the gas can be changed. If the balance is initially balanced with nitrogen in that chamber, and then the chamber is filled with oxygen, the paramagnetic oxygen gas is attracted to the stronger part of the magnetic field and the body rotates. The twist in the suspension is usually detected by an optical lever system.

Haven, who measured the magnetic susceptibility of gases, experimented with different shapes for the test body. His conclusion was that dumb-bell shape was the most suitable. This became the standard shape used by experimenters using the Faraday method. Early patents on such devices are U.S. Pat. No. 2,416,344 Pauling, U.S. Pat. No. 2,666,893 Munday, U.S. Pat. No. 2,744,234 Munday et al, U.S. Pat. No. 2,962,656 Munday.

The Munday cell became the most used paramagnetic oxygen sensor and in its modern form will consist basically of a small dumb-bell test body. Glass spheres (usually about 3 mm diam) filled with pure nitrogen are joined to make the dumb-bell. A single turn coil and a mirror are cemented to the dumbbell and suspended through a very thin strip of platinum iridium alloy in a non uniform magnetic field. The field is generated by strong magnets which are part of a magnetic circuit into which the cell is pushed and held in position.

The magnetic field inside the cell is shaped by the shape of the pole pieces. The dumbbell being diamagnetic, takes up a position away from the most intense part of the magnetic field. The cell is a gas chamber which has a front window so as to allow the movement of the dumb-bell to be monitored, and houses the pole pieces and the test body and is sealed gas tight with epoxy. Electric pins in the back of the cell allow an electric current to pass through the suspension strip, round the single turn feedback coil and out through the bottom half of the suspension strip and lower electric pin. Gas is admitted via gas connectors ending with nozzles. The gas impinges on the inner wall of the cell and the nozzle has to be oriented so that the flow produces a minimum disturbance to the dumb-bell (flow errors).

When the gas surrounding the dumb-bell is diamagnetic, eg nitrogen; the dumb-bell will take a certain position (the null position); if this gas is now changed to a paramagnetic gas such as oxygen, for example, the dumb-bell will be deflected. This deflection is detected by the optical system, which comprises a light beam which is shone onto the mirror at the centre of the dumb-bell, and is reflected to a pair of photocells which are arranged in opposition and placed such that their output is zero when nitrogen is inside the cell. When the dumb-bell is deflected due to the presence of a paramagnetic gas in the chamber, this is picked up by the photocells and their signal is amplified and fed back to the cell via the coil round the dumb-bell. The current has such a polarity that when it interacts with the magnetic field present it produces a restoring torque of the dumb-bell which comes into equilibrium when the dumb-bell returns to the original null (nitrogen) position.

By calibrating the system with a gas of known concentration, the feedback current will be proportional to the partial pressure of oxygen in the gas mixture admitted to the cell.

At typical conditions such equipment is run at 150 ml/min gas flow rate. The volume of the cell is of the order of 3.5 ml.

In some applications where it is necessary to detect a particular gas in a mixture, for example in medical applications such as pulmonary functions and aneasthesia, the amount of gas sample that can be taken over a period of time is limited. For example, in pulmonary function and anaesthesia applications the amount of gas which can be taken from the patient is limited to only about 50 ml/min. In such applications it may also be desirable that the particular gas sensor apparatus have a fast response time for analysis. In pulmonary function and anaesthesia applications, for example, it is desirable to be able to analyse the breath of a patient breathing at a rate of 30 breaths per minute. This requires the sensor to have a response time of the order of 0.5 seconds at a gas flow rate of about 50 ml/min so as to achieve a reasonable accuracy during the analysis of the data. Such prior art gas testing apparatus as described above cannot satisfy these requirements. Tests on commercially available sensors which have internal volumes of the order of 3.5 ml, at a gas flow rate of 50 ml/min give responses with a time constant (T 63.2%) in the region of 3 to 5 seconds. This is unsatisfactory.

We have found that the desired response can be achieved, at the low gas flow rates necessary, by providing a gas flow sensor where the chamber housing the test body, through which the gas must flow, is of very small volume.

The present invention provides gas testing apparatus, comprising a body defining a chamber therein, a test body mounted within the chamber for movement in a magnetic field, and means for allowing gas to flow through the chamber wherein the chamber has a volume of less than 0.6 ml.

The small chamber size is preferably achieved by casting or moulding the body which defines the chamber. The body is preferably cast mounting the elements forming a magnetic circuit to provide the magnetic field (eg magnets, magnetic frame, pole pieces).

Such materials as epoxy or plastics may be used for the body.

A two piece construction is preferred for the apparatus. For example, it is preferred that the body consists of a main part and a cover part, which are mechanically joined to form the body defining the chamber.

From a further aspect the present invention provides a gas testing apparatus, comprising a body defining a chamber therein, a test body mounted with the chamber for movement in a magnetic field, and means for allowing gas to flow through the chamber, the body comprising two parts, a main part and a cover part which are arranged to be mechanically joined together in a sealable manner to define the chamber.

Because of the fast response times desired the actual rate of gas exchange within the test chamber must be rapid, even where the actual gas volume flow rate is low. This means that the gas flow velocity through the chamber is higher than normal for such apparatus. A problem is that the test body in such apparatus is so sensitive that the physical flow of gas impinging thereon introduces errors by causing motion of the test body (flow errors). Where the gas flow velocity through the chamber is high the chances of introducing large magnitude flow errors are also high. From a further aspect the present invention provides an apparatus where the gas flow regime is designed to produce minimal flow errors.

The present invention further provides a gas testing apparatus, comprising a body defining a chamber therein, a test body mounted within the chamber for movement in a magnetic field, and gas inlet and outlet means for allowing gas flow through the chamber, the gas inlet means being arranged such that gas approaches the chamber and test body symmetrically, from either side thereof, the gas flows meeting at the centre of the chamber where the test body is suspended and cancelling out by the opposition in flow any forces which may cause undesired motion of the test body.

In a preferred embodiment, channels through which the gas flow approaches the chamber are defined on one side by fins. These fins are preferably shaped aerodynamically so as to bend the gas flow to ensure a good flush of the gas chamber. They are preferably curved so that the gas flow channels broaden out in one plane as the approach the chamber.

The test body is preferably suspended in the chamber by a suspending wire, and the gas flow preferably is arranged to run down the channels in which the suspending wire runs.

The present invention yet further provides a gas testing apparatus, comprising a body defining a chamber therein, a test body mounted within the chamber for movement in a magnetic field, and gas inlet and outlet means for allowing gas flow through the chamber, restrictor means being provided at the outlet to ensure that the chamber is completely swept by the gas.

The present invention yet further provides a gas testing apparatus, comprising a body defining a chamber therein, a test body mounted by a suspending wire in the chamber for movement in a magnetic field, and gas inlet and outlet means for allowing gas flow through the chamber, wherein the suspending wire is mounted on springs either side of the chamber, and wherein the gas inlet means are directed at the springs in order to sweep the dead spaces around the springs with gas.

The gas testing apparatus has the advantage that accurate gas detection (eg of oxygen) can be made at fast response times with low gas flow rates.

Features and advantages of the present invention will become apparent from the following description of an embodiment thereof, by way of example only, with reference to the accompanying drawings, in which.

Figure 2:
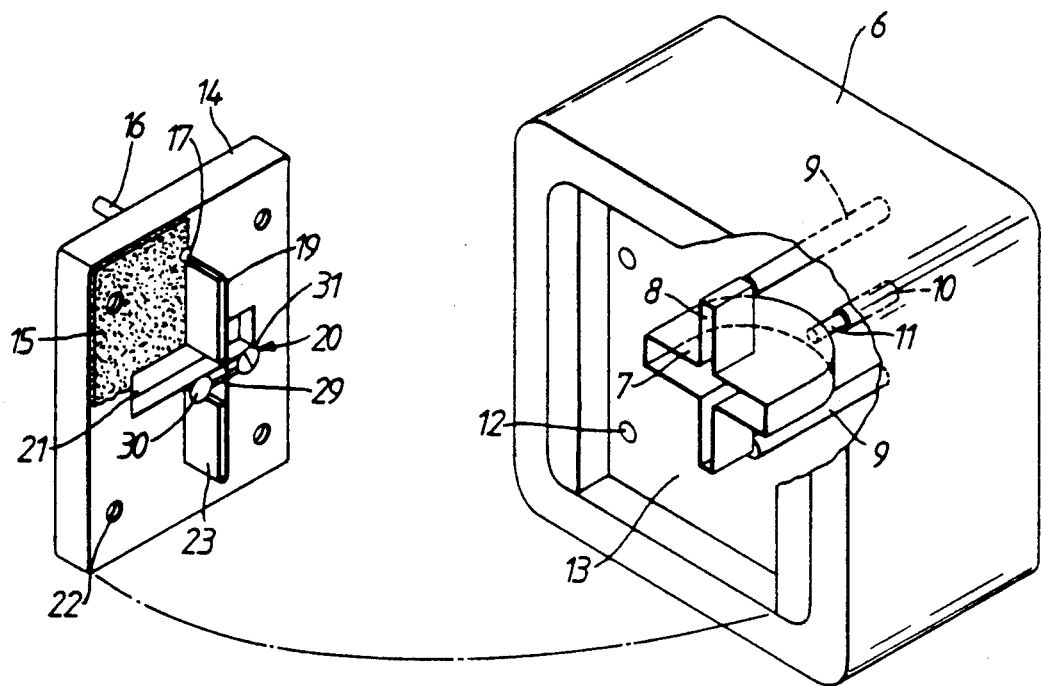
FIG. 2 shows a perspective view of a two piece gas testing apparatus in accordance with an embodiment of the present invention.

We have found that under perfect sweep conditions at a flow rate of 50 ml/min the volume of the gas chamber of the sensor has to be of the order of 0.5 ml so as to achieve the required response time. A standard test body of FIG. 2 is used comprising a dumb-bell 31, a mirror 29, a feedback coil 30 and a suspension strip 19.

Figure 1:
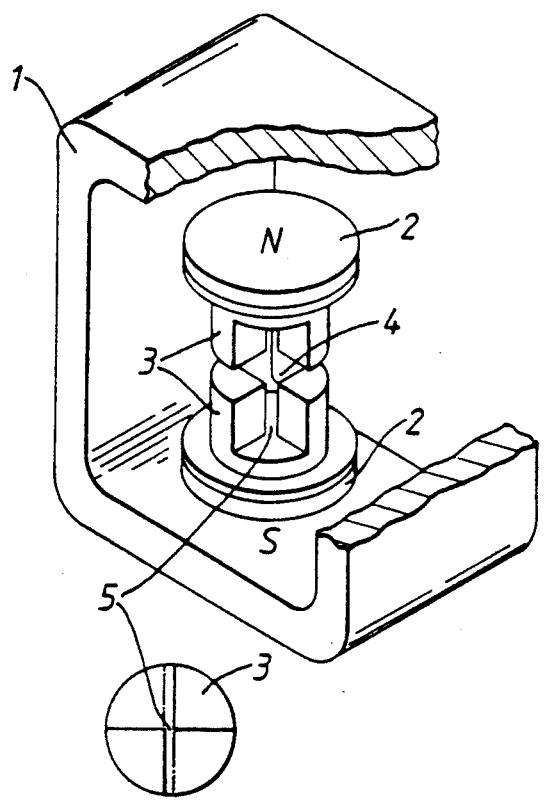
FIG. 1 shows a perspective view of a magnetic circuit in accordance with an embodiment of the present invention.
Figure 3:
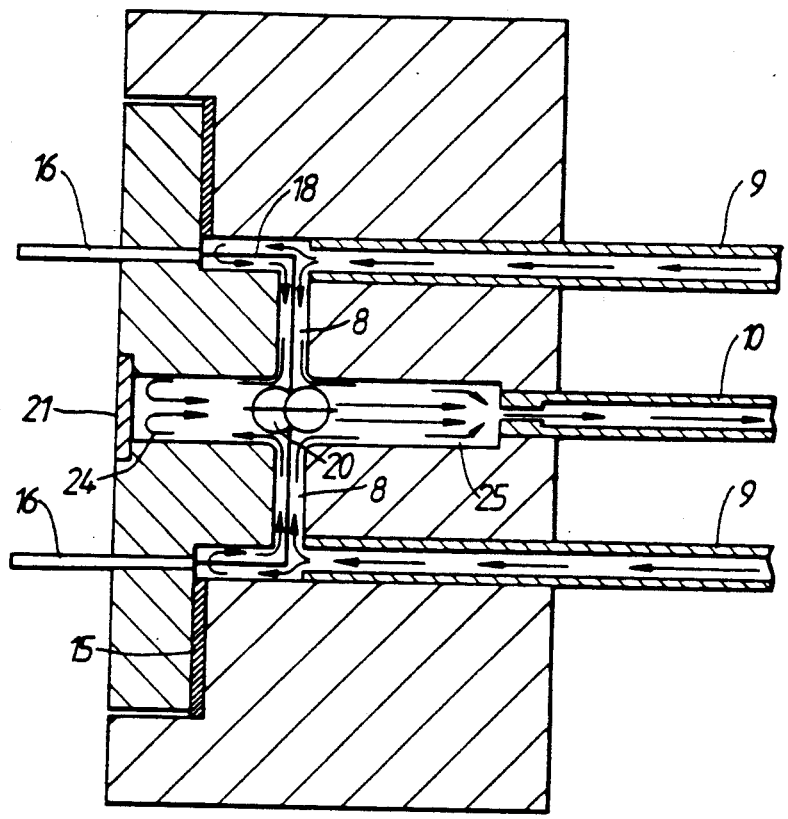
FIG. 3 shows a cross section through the assembled apparatus of FIG. 2 illustrating the gas flow regime.

The magnetic field required to surround the test body 20 is provided by a miniature magnetic circuit as shown in FIG. 1. Iron boron or rare earth cobalt magnets ensure a very small volume of magnet 2 with acceptable field strength, the magnetic circuit is completed with a soft magnetic material frame 1 of appropriate dimensions to which the magnets 2 are stuck. The magnetic field is concentrated and shaped by appropriate pole pieces 3, made from soft magnetic material, produce in the space 4 between the upper and lower pole piece regions of strong magnetic field and very high gradient. This is the region where the test body 20 is positioned and hangs suspended by its strip 19 along a channel 5 cut in the pole pieces 3. The pole pieces 3 are stuck with adhesive to the magnets 2 in the correct orientation. In order to minimise the volume of the gas chamber, only the necessary volumes are created. This can be achieved by casting the frame in an appropriate casting material such as an epoxy, or the use of plastics. The required shape is seen in FIG. 2. The frame 6 is filled with a potting compound with the exception of the gas chamber area which consists of a nearly circular part 7 where the test body 20 hangs suspended by the suspension strip 19, and is able to move freely around its centre. The metallic strip 19 hangs in the channel 8. The channel 8 receives from the back the two gas inlet tubes 9 through which the test gas is admitted into the chamber 7. The outlet pipe 10 which has a restricted part 11 is positioned at the centre of the main chamber 7 at the back. The three pipes 10, 9 and four screws studs 12 are potted in the main frame 6 with the potting compound or plastic moulding 13. The front of this part now presents a flat face into which the front of the assembly 14 fits and is sealed thereto by means of a thin gasket 15 tightened to effect a seal with screws through four holes 22. Note that the gasket 15 covers the whole face of the part 14, and is not all shown in FIG. 2. The front is cast in a plastic or epoxy and has as inserts pins which provide an electrical connection to the feedback coil 30 which is on the test body 20 via the springs 18 and the suspension strip 19. The point of emergence of the spring 17 is gas tight either by sealing or by the inclusion of he pins during moulding the front 14. The front 14 has an aperture to which a gas tight glass window 21 is fixed. This enables the light to enter the chamber get reflected on the mirror 20 at the centre of the test body, and again exit through the window 21 so as to arrive at the photocells of the optical detection apparatus. Fins 23 cast as part of 14 ensure that the slot 8 is filled and has only the minimum of volume. Once the front 14 is sealed to the back, the gas chamber 7 with the test body 20 inside sitting in the correct position relative to the magnetic field, is flushed by admitting the sample gas simultaneously from inlets 9 and letting the outgoing gas through the outlet 10. The optical system used to detect the position of the test body and the electronic feed back system used to maintain the test body in the null position are similar to the standard systems used with such devices as described earlier. Referring to FIG. 3 which shows a schematic of the gas flow circuit of the sensor within the gas chamber, two inlet pipes 9 are used in a symmetrical configuration so as to sweep the upper and lower part of the chamber 7 and also not disturb the test body 20 by virtue of halving the speed of the gas impingeing on the dumb-bell 31 and equalising it by the simultaneous arrival from both sides. The inlet pipes are also positioned so as to admit the gas directly aimed at the spring 18 to which the suspension strip 19 is welded and which is situated in a very small space. The incoming gas turns and runs along the channel 8 which houses the suspension strip 19. Upon arrival to the middle part of the chamber, the gas turns towards the outlet pipe 10 and emerges out of the chamber. The outlet includes a restrictor 11 which is chosen so as to stop the immediate turning of the gas to the outlet after its emergence from the channels 8 and thus leaving the gas in the front of the mid chamber 24 to exchange by diffusion which is slow. When the restrictor is chosen correctly the pressure build up in the rear part of the mid chamber 25 ensures that part of the gas turns towards the front part 24 and sweeps it and thus a fast response time achieved.

As an example, for fast response applications, we have found with this embodiment that an optimum size of inlet restrictions is 1 mm id and that for the outlet is 0.7 mm. The volume of the cell is not greater than 0.5 ml which together with the optimum flow regime described above gives a 0-63% time response not greater than 500 ms and a 10-90% time response not greater than 900 ms when the gas flow rate is 50 ml/ in. These values are recorded for a positive step change in oxygen concentration occuring at the inlet of the cell. Eg switching from nitrogen to air.

Figure 4:
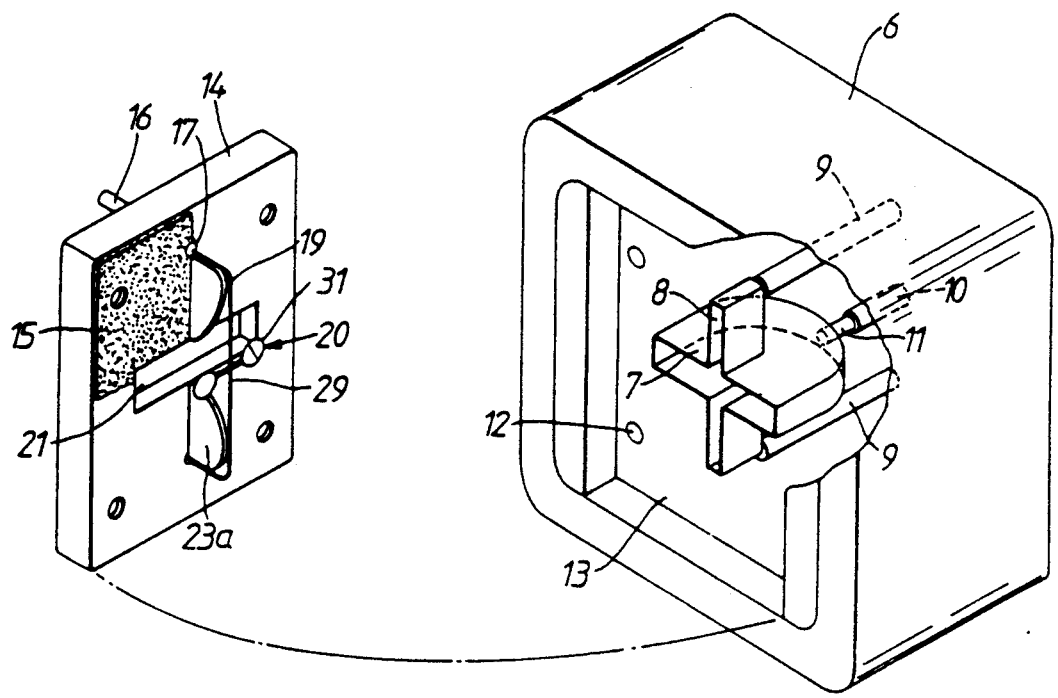
FIG. 4 shows a perspective view of a two piece gas testing apparatus in accordance with a further embodiment of the present invention.
Figure 5:
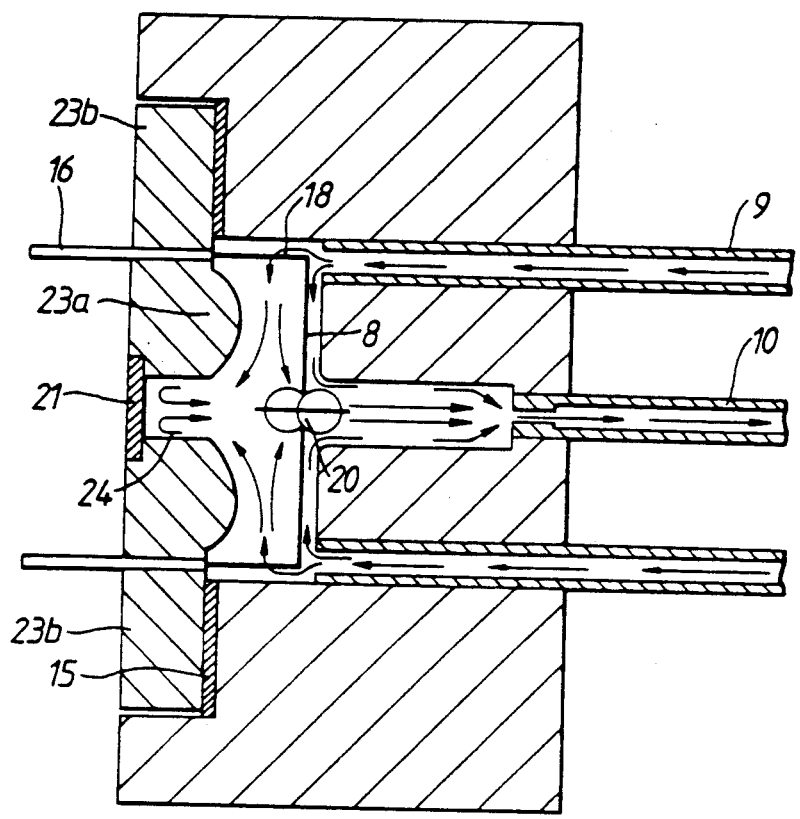
FIG. 5 shows a cross section through the assembled apparatus of FIG. 4 illustrating the gas flow regime.

FIGS. 4 and 5 illustrate a further embodiment of the present invention, wherein the gas flow regime is improved by the utilisation of specially shaped fins 23a. The same reference numerals are used in these Figures for parts which are the same for the embodiment of FIGS. 2 and 3.

The fins 23a do not fill the channels 8, as in the previous embodiment. Instead, they are aerodynamically shaped so as to bend the gas flow towards the window, ensuring thus a good flush of the chamber 7. The channels effectively broaden in a direction towards the window as the chamber 7 is approached.

FIGS. 4 and 5 show that the fins can be provided with extentions 23b arranged to be received in corresponding grooves 8a of the channels 8. These extensions 23b and grooves 8a are dimensioned to ensure that when the assembly 14 shown in FIGS. 2 and 4 is fitted on to the moulding 13, the test body will be accurately located at the correct position within the chamber 7. The extensions also serve to guide the two parts forming the apparatus and so reduce potential damage to the suspension and test body during assembly.

We claim:

1. A gas testing apparatus comprising a body (13, 14) defining a chamber (7), means (2,3) for creating a magnetic filed within the chamber in a first direction, a test body (20), means (19) for mounting the test body (20) in said chamber (7) for rotation about an axis parallel to the direction of the magnetic field, and gas inlet (9) and outlet (10) means for allowing gas flow through the chamber (7), characterized in the the gas inlet means (9) are arranged and disposed to supply gas to the chamber (7) from two positions at opposite sides of the chamber whereby gas flow from each of the two positions will be parallel to the direction of the magnetic field but in opposition in order to minimize errors resulting from gas flow upon the test body 20.

2. Apparatus according to claim 1 wherein the outlet means (10) is located midway between the two inlet positions.

3. Apparatus according to claim 1 or 2, wherein the body is formed in two parts (13, 14), one body part (14) defining the shape of the chamber (7) and the other part (13) being provided with the mounting means (19) and the test body (20) and forming a cover for the chamber (7).

4. Apparatus according to claim 3, wherein the chamber (7) is constituted by two pair of opposed grooves (8) forming a cruciform cross-sectional shape, one pair of said two pair of opposed grooves receiving the means (19) for mounting the test body (20) and the other pair of said two pair of opposed grooves receiving the test body (20) as it rotates, in use, the gas inlets means (9) opening into the grooves.

5. Apparatus according to claim 4, and comprising fins (23, 23a) provided on the other body part (13) and disposed to be received into the first pair of opposed grooves (8) in the said one body part (14).

6. Apparatus according to claim 5, wherein the fins (23a) are aerodynamically shaped whereby to ensure flushing of the chamber.

7. Apparatus according to claim 1, wherein the chamber has a volume of less than 0.6 ml.

8. Apparatus according to claim 5, wherein the fins (23, 23a) include extensions (23b) which are dimensioned so as to ensure that when the fins are inserted into the first pair of said two pair of opposed grooves (8) the means (19) for mounting the test body 20 and the test body (20) are correctly located in the chamber (7).

* * * * *